United States Patent
Wang et al.

(10) Patent No.: US 7,611,898 B2
(45) Date of Patent: Nov. 3, 2009

(54) AGROBACTERIUM TRANSFORMATION OF STOLONS

(75) Inventors: Zengyu Wang, Ardmore, OK (US); Yaxin Ge, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 0 days.

(21) Appl. No.: 11/431,142

(22) Filed: May 9, 2006

(65) Prior Publication Data

US 2007/0044173 A1 Feb. 22, 2007

Related U.S. Application Data

(60) Provisional application No. 60/679,023, filed on May 9, 2005.

(51) Int. Cl.
*C12N 15/82* (2006.01)
*C12N 15/87* (2006.01)

(52) U.S. Cl. .................. 435/469; 435/468; 800/278

(58) Field of Classification Search .............. None
See application file for complete search history.

(56) References Cited

U.S. PATENT DOCUMENTS

| | | | |
|---|---|---|---|
| 4,795,855 A | 1/1989 | Fillatti et al. | 800/288 |
| 4,954,442 A | 9/1990 | Gelvin et al. | 435/469 |
| 5,004,863 A | 4/1991 | Umbeck | 800/314 |
| 5,159,135 A | 10/1992 | Umbeck | 800/314 |
| 5,188,958 A | 2/1993 | Moloney et al. | 800/300 |
| 5,262,316 A | 11/1993 | Engler et al. | 800/294 |
| 5,416,011 A | 5/1995 | Hinchee et al. | 800/294 |
| 5,463,174 A | 10/1995 | Moloney et al. | 800/294 |
| 5,530,182 A | 6/1996 | Sondahl et al. | 435/430.1 |
| 5,563,055 A | 10/1996 | Townsend et al. | 800/294 |
| 5,565,347 A | 10/1996 | Fillatti et al. | 800/294 |
| 5,569,834 A | 10/1996 | Hinchee et al. | 800/312 |
| 5,589,615 A | 12/1996 | De Clercq et al. | 800/298 |
| 5,591,616 A | 1/1997 | Hiei et al. | 435/469 |
| 5,689,053 A | 11/1997 | Robert et al. | 800/287 |
| 5,693,512 A | 12/1997 | Finer et al. | 435/173.5 |
| 5,712,112 A | 1/1998 | Yu et al. | 435/69.1 |
| 5,733,744 A | 3/1998 | Hamilton | 435/69.1 |
| 5,750,871 A | 5/1998 | Moloney et al. | 800/294 |
| 5,824,872 A | 10/1998 | Miki et al. | 800/278 |
| 5,824,877 A | 10/1998 | Hinchee et al. | 800/294 |
| 5,846,797 A | 12/1998 | Strickland | 800/294 |
| 5,919,919 A | 7/1999 | Robert et al. | 800/287 |
| 5,922,928 A | 7/1999 | Chiang et al. | 800/278 |
| 5,929,300 A | 7/1999 | Burke et al. | 800/278 |
| 5,932,782 A | 8/1999 | Bidney | 800/293 |
| 5,948,956 A | 9/1999 | Lee et al. | 800/320 |
| 5,952,543 A | 9/1999 | Fioozabady et al. | 800/294 |
| 5,977,439 A | 11/1999 | Hamilton | 800/294 |
| 5,981,840 A | 11/1999 | Zhao et al. | 800/294 |
| 5,994,624 A | 11/1999 | Trolinder et al. | 800/278 |
| 6,037,522 A | 3/2000 | Dong et al. | 800/278 |
| 6,040,498 A | 3/2000 | Stomp et al. | 800/294 |
| 6,051,757 A | 4/2000 | Barton et al. | 800/294 |
| 6,074,876 A | 6/2000 | De Block | 435/468 |
| 6,074,877 A | 6/2000 | D'Halluin et al. | 435/468 |
| 6,103,955 A | 8/2000 | Pena Garcia et al. | 800/294 |
| 6,162,965 A | 12/2000 | Hansen | 800/278 |
| 6,215,051 B1 | 4/2001 | Yu et al. | 800/320.2 |
| 6,255,115 B1 | 7/2001 | Beijersbergen et al. | 435/477 |
| 6,255,559 B1 | 7/2001 | Cheah | 800/278 |
| 6,265,638 B1 | 7/2001 | Bidney et al. | 800/294 |
| 6,274,791 B1 | 8/2001 | Dhir et al. | 800/294 |
| 6,300,545 B1 | 10/2001 | Baszczynski et al. | 800/294 |
| 6,307,127 B1 | 10/2001 | Jøreboe et al. | 800/294 |
| 6,323,396 B1 | 11/2001 | Dirks et al. | 800/294 |
| 6,369,298 B1 | 4/2002 | Cai et al. | 800/294 |
| 6,384,301 B1 | 5/2002 | Martinell et al. | 800/294 |
| 6,420,630 B1 | 7/2002 | Wilson et al. | 800/294 |
| 6,455,761 B1 | 9/2002 | Kuvshinov et al. | 800/294 |
| 6,603,061 B1 | 8/2003 | Armstrong et al. | 800/294 |
| 6,620,986 B1 | 9/2003 | McKeon et al. | 800/294 |
| 6,664,108 B1 | 12/2003 | Baszczynski et al. | 435/469 |
| 6,686,515 B1 | 2/2004 | Lassner et al. | 800/294 |

(Continued)

FOREIGN PATENT DOCUMENTS

JP 2004-201509 7/2004

(Continued)

OTHER PUBLICATIONS

Hansen et. al., 1999, Trends in plant Science, vol. 4, pp. 226-231.*

(Continued)

*Primary Examiner*—Ashwin Mehta
*Assistant Examiner*—Li Zheng
(74) *Attorney, Agent, or Firm*—Steven P. Rhines, Esq.; Sonnenschein Nath & Rosenthal LLP

(57) ABSTRACT

The invention provides methods for transforming monocotyledonous plants with *Agrobacterium*, for example, using stolons as a target tissue. The invention allows creation of transgenic plants without the need for callus as a target tissue for transformation, thus providing a rapid method for the production of transgenic plants. The ability to directly regenerate transgenic plants from stolons significantly reduces the time, labor and other complications required to produce transgenic plants. Plants produced by such methods are also provided by the invention.

16 Claims, 3 Drawing Sheets

U.S. PATENT DOCUMENTS

| | | | |
|---|---|---|---|
| 6,696,622 B1 | 2/2004 | Gelvin et al. | 800/294 |
| 6,759,573 B2 | 7/2004 | Olhoft et al. | 800/294 |
| 6,800,791 B1 | 10/2004 | Bailey et al. | 800/278 |
| 6,822,144 B1 | 11/2004 | Zhao et al. | 800/320.1 |
| 6,846,971 B1 | 1/2005 | Xie et al. | 800/294 |
| 2006/0156443 A1* | 7/2006 | Rommens et al. | 800/294 |

FOREIGN PATENT DOCUMENTS

| | | |
|---|---|---|
| JP | 2005-137291 | 6/2005 |

OTHER PUBLICATIONS

White et al. 1987, Plant Molecular Biology 8:461-469.*
Zhang et al. 2003, Plant Cell Rep. 21:860-864.*
Aldemita and Hodges, "*Agrobacterium tumefaciens*-mediated transformation of japonica and indica rice varieties," *Planta*, 199:612-617, 1996.
Bond and Webb, "Regeneration and analysis of plants from stolon segments of *Trifolium repens* (white clover)," *Plant Science*, 61:119-126, 1989.
Cheng et al., "Desiccation of plant tissues post-*Agrobacterium* infection enhances T-DNA delivery and increases stable transformation efficiency in wheat," In Vitro *Cell. Dev. Biol.—Plant*, 39, 595-604, 2003.
Cheng et al., "Invited review: Factors influencing *Agrobacterium*-mediated transformation of monocotyledonous species," In Vitro *Cell. Dev. Biol.—Plant*, 40, 31-45, 2004.
Cho et al., "Transformed T0 orchardgrass (*Dactylis glomerata* L.) plants produced from highly regenerative tissues derived from mature seeds," *Plant Cell Rep.*, 20:318-324, 2001.
Choi et al., "Increased Chromosomal Variation in Transgenic versus Nontransgenic Barley (*Hordeum vulgare* L.) Plants," *Crop Sci.*, 40:524-533, 2000.
Dai et al., "Comparative analysis of transgenic rice plants obtained by *Agrobacterium*-mediated transformation and particle bombardment," *Mol. Breed.*, 7:25-33, 2001.
Dai et al., "Expression of pokeweed antiviral proteins in creeping bentgrass," *Plant Cell Rep.*, 21:497-502, 2003.
Frame et al., "*Agrobacterium tumefaciens*-Mediated Transformation of Maize Embryos Using a Standard Binary Vector System," *Plant Physiol.*, 129:13-22, 2002.
Ge et al., "Transgenic zoyiagrass (*Zoysia japonica*) plants obtained by *Agrobacterium*-mediated transformation," *Plant Cell Reports*, 25:792-798, 2006.
Goldman et al., "Ploidy variation among herbicide-resistant bermudagrass plants of cv. TifEagle transformed with the bar gene," *Plant Cell Rep.*, 22:553-560, 2004.
Hartman et al., "Herbicide Resistant Turfgrass (*Agrostis palustris* Huds.) by Biolistic Transformation," *Bio/Technology*, 12:919-923, 1994.
Hiei et al., "Transformation of rice mediated by *Agrobacterium tumefaciens*," *Plant Mol. Biol.*, 35(1-2):205-218, 1997.
Hu et al., "*Agrobacterium*-mediated large-scale transformation of wheat (*Triticum aestivum* L.) using glyphosate selection," *Plant Cell Rep.*, 21:1010-1019, 2003.
Hu et al., "*Agrobacterium*-mediated transformed transgenic triploid bermudagrass (*Cynodon dactylon* X C. transvaalensis) plants are highly resistant to the glufosinate herbicide Liberty," *Plant Cell Tissue and Organ Culture*, 83:13-19, 2005.
Huber et al., "High transformation frequencies obtained from a commercial wheat (*Triticum aestivum* L. cv. 'Combi') by microbombardment of immature embryos followed by GFP screening combined with PPT selection," *Mol. Breed.*, 10:19-30, 2002.
Ishidia et al., "High efficiency transformation of maize (*Zea mays* L.) mediated by *Agrobacterium tumefaciens*," *Nat. Biotechnol.*, 14(6):745-750, 1996.
Janakiraman, et al., "Recent advances in wheat transformation," In Vitro *Cell. Dev. Biol.—Plant*, 38:404-414, 2002.
Li and Qu, "Development of highly regenerable callus lines and biolistic transformation of turf-type common bermudagrass [*Cynodon dactylon* (L.) Pers.]," *Plant Cell Rep.*, 22:403-407, 2004.

Luo et al., "*Agrobacterium tumefaciens*-mediated creeping bentgrass (*Agrostis stolonifera* L.) transformation using phosphinothricin selection results in a high frequency of single-copy transgene integration," *Plant Cell Rep.*, 22:645-652, 2004.
McCormac et al., "The use of visual marker genes as cell-specific reporters of *Agrobacterium*-mediated T-DNA delivery to wheat (*Triticum aestivum* L.) and barley (*Hordeum vulgare* L.)," *Euphytica*, 99(1):17-25, 1998.
Popelka and Altpeter, "*Agrobacterium tumefaciens*-mediated genetic transformation of rye (*Secale cereale* L.)," *Mol. Breed.*, 11:203-211, 2003.
Potrykus, "Gene Transfer to Plants: Assessment of Published Approaches and Results<" *Annu. Rev. Plant Physiol. Plant Mol. Biol.*, 42:205-225, 1991.
Sallaud et al, "Highly efficient production and characterization of T-DNA plants of rice (*Oryza sativa* L.) functional genomics," *Theor. Appl. Genet.*, 106:1396-1408, 2003.
Spangenberg et al., "Transgenic Tall Fescue (*Festuca arundinacea*) and Red Fescue (*F. rubra*) Plants from Microprojectile Bombardment of Embryogenic Suspension Cells," *J. Plant Physiol.*, 145:693-701, 1995.
Spangenberg et al., In: *Biotechnology in forage and turf grass improvement*, Springer, Berlin, (Frankel et al. eds.), 1998.
Thomas et al., "Selection of Interspecific Somatic Hybrids of Medicago by using *Agrobacterium*-transformed tissues," *Plant Sci.* 69:189-198, 1990.
Tingay et al., "*Agrobacterium tumefaciens*-mediated barley transformation," *Plant J.*, 11(6):1369-1376, 1997.
Toyama et al., "Production of Herbicide-tolerant Zoysiagrass by *Agrobacterium*-mediated Transformation," *Mol. Cells.* 16:19-27, 2003.
Vasil et al., "Herbicide resistant fertile transgenic wheat plants obtained by microprojectile bombardment of regenerable embryogenic callus," *Bio/Technology*, 10:667-674, 1992.
Wan and Lemaux, "Generation of Large Numbers of Independently Transformed Fertile Barley Plants," *Plant Physiol.*, 104:37-48, 1994.
Wang and Ge, "*Agrobacterium*-mediated high efficiency transformation of tall fescue (*Festuca arundinacea*)," *J. Plant Physiol.*, 162:103-113, 2005.
Wang and Ge, "Rapid and efficient production of transgenic bermudagrass and creeping bentgrass bypassing the callus formation phase," *Functional Plant Biology*, 32:769-776, 2005.
Wang et al., "Characterization of cis-Acting Elements Regulating Transcription from the Promoter of a Constitutively Active Rice Actin Gene," *Molec. Cell. Biol.*,12(8):3399-3406, 1992.
Wang et al., "Development of an efficient plant regeneration system for Russian wildrye (*Psathyrostachys juncea*)," *Plant Cell Rep.*, 20:797-801, 2002.
Wang et al., "Establishment of a plant regeneration system for wheatgrasses (*Thinopyrum, Agropyron and Pascopyrum*)," *Plant Cell, Tissue Organ Cult.*, 73:265-273, 2003.
Wang et al., "Forage and Turf Grass Biotechnology," *Crit. Rev. Plant Sci.*, 20:573-619, 2001.
Wang et al., "Inheritance of transgenes in transgenic tall fescue (*Festuca Arundinacea* Schreb.)," In Vitro *Cell. Dev. Biol. Plant*, 39:277-282, 2003.
Wang et al., "Transgenic Russian wildrye (*Psathyrostachys juncea*) plants obtained by biolistic transformation of embryogenic suspension cells," *Plant Cell Rep.*, 22:903-909, 2004.
White and Greenwood, "Transformation of the forage legume *Trifolium repens* L. using binary *Agrobacterium* vectors," *Plant Mol. Biol.*, 8:461-469, 1987.
Wuersig, "An overview of stolon and cotyledon transformation in White Clover (*Trifolium repens*)," Online, https://www.noble.org/summerscholar/2004presentations/renate/index_files/frame.html, 2004.
Xiao et al., "Efficient selection and regeneration of creeping bentgrass transformants following particle bombardment," *Plant Cell Rep.*, 16:874-878, 1997.
Ye et al., "Transgenic Italian ryegrass (*Lolium multiflorum*) plants from microprojectile bombardment of embryogenic suspension cells," *Plant Cell Rep.*, 16:379-384, 1997.

Yu et al., "*Agrobacterium*-mediated transformation of creeping bentgras using GFP as a reporter gene," *Hereditas*, 133:229-233, 2000.

Zhang et al., "Transformation of triploid bermudagrass (*Cyondon dactylon* X C. transvaalensis cv. TifEagle) by means of biolistic bombardment," *Plant Cell Rep.*, 21:860-864, 2003.

Zhao et al., "*Agrobacterium*-mediated sorghum transformation," *Plant Mol. Biol.*, 44:789-798, 2000.

Zhong et al., "Transgenic plants of turfgrass (*Agrostis palustris* Huds.) from microprojectile bombardment of embryogenic callus," *Plant Cell Rep.*, 13:1-6, 1994.

Zilinskas, "The role of biotechnology in improving turfgrass performance," 2000 Rutgers Turfgrass Proceedings Jul. 2001, vol. 32, 2001.

* cited by examiner

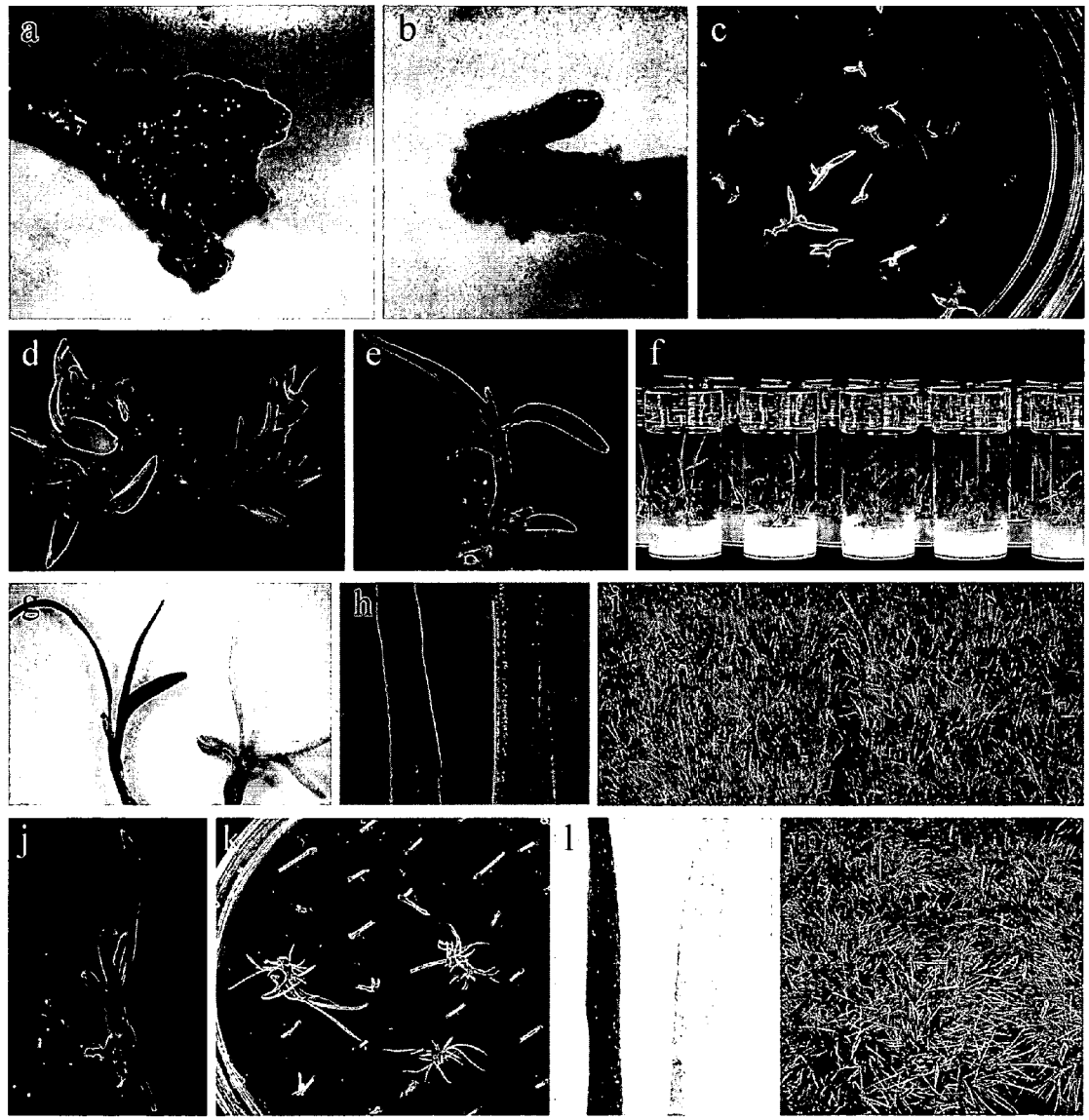
FIG. 1A-M

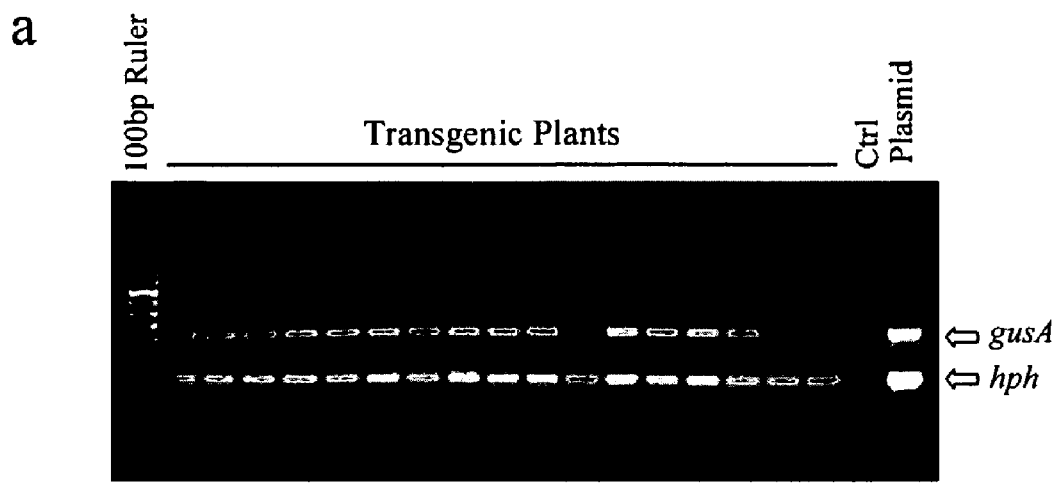
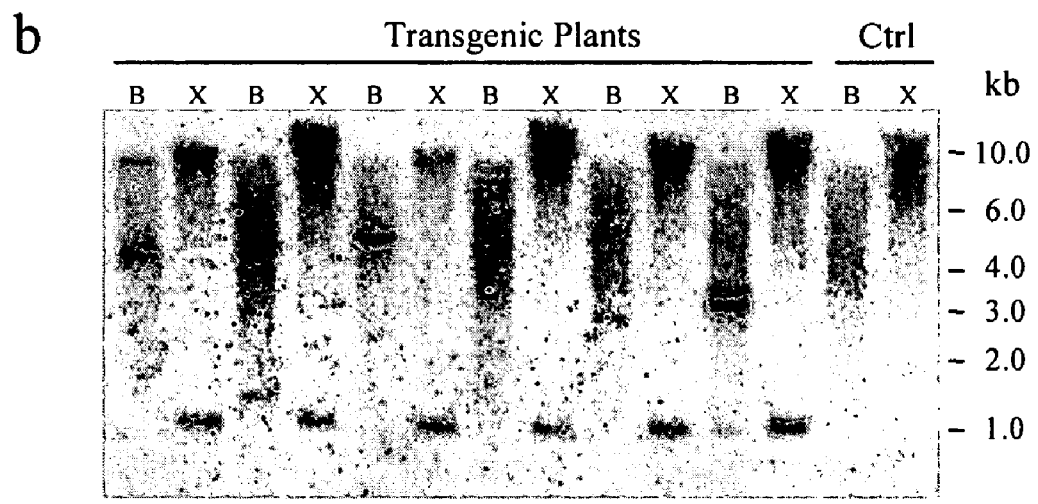
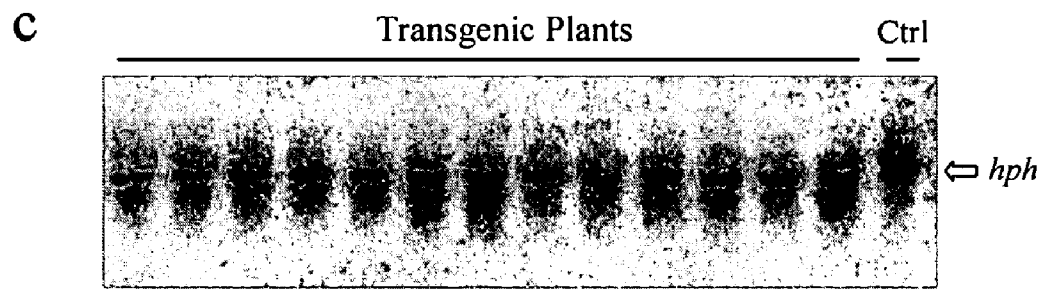
FIG. 2A-C

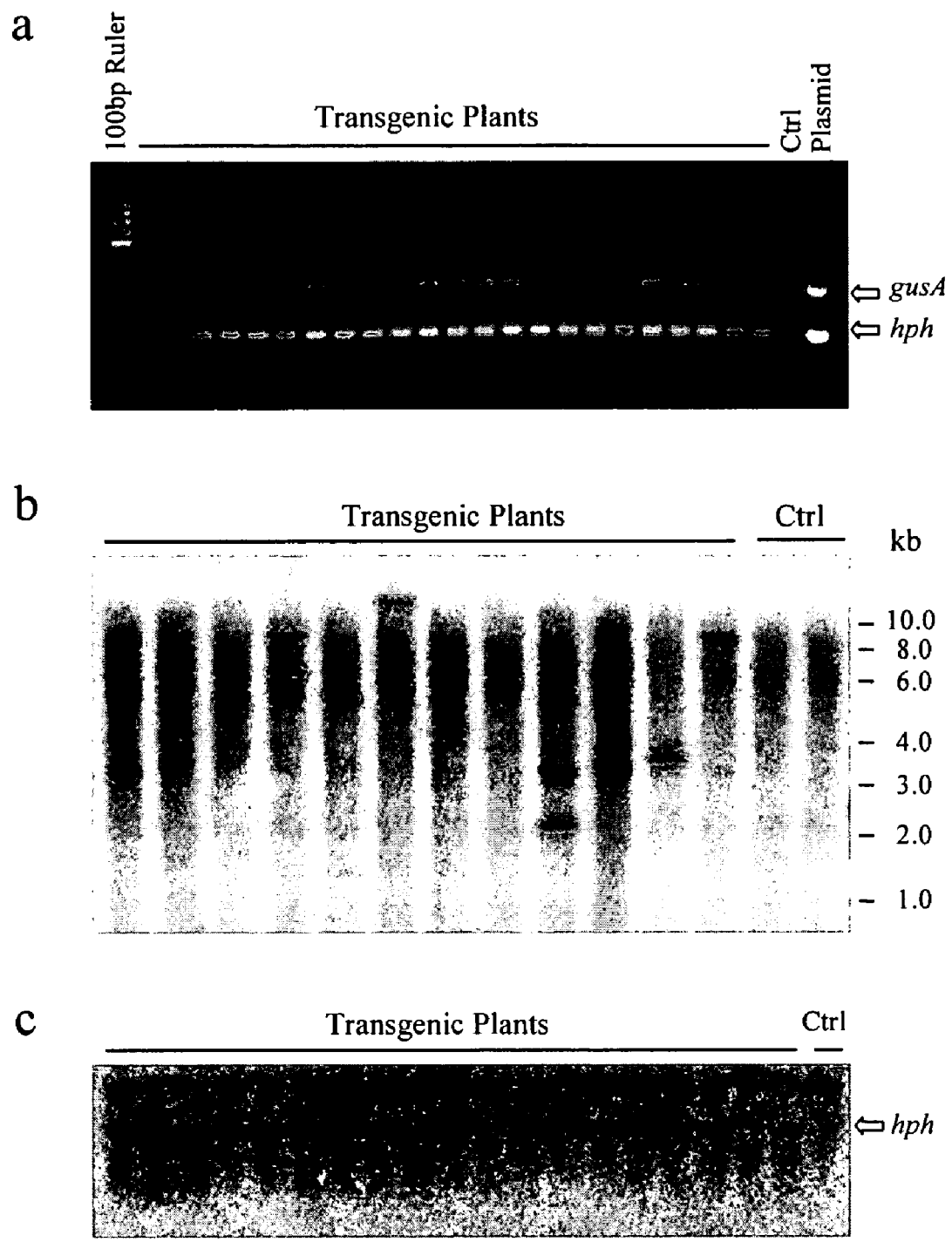
FIG. 3A-C

AGROBACTERIUM TRANSFORMATION OF STOLONS

This application claims the priority of U.S. Provisional Application Ser. No. 60/679,023, filed May 9, 2005, the entire disclosure of which is incorporated herein by reference.

BACKGROUND OF THE INVENTION

1. Field of the Invention

The present invention relates generally to the fields of botany and molecular biology. More specifically, the invention relates to plant transformation using *Agrobacterium*-mediated gene transfer into the stolon of plants.

2. Description of the Related Art

Forage and turf grasses are the backbone of sustainable agriculture and contribute extensively to the world economy. On a worldwide basis, grassland acreage is estimated to be twice that of cropland (Jauhar, 1993). Along with cereal crops, these monocotyledonous (monocot) species have been considered recalcitrant for genetic transformation (Ke et al., 2001; Sahrawat et al., 2003; Spangenberg et al., 1998; Vasil, 1994). Transgenic monocot plants were first obtained by direct gene transfer to protoplasts, then by biolistic transformation, and in more recent years by *Agrobacterium*-mediated transformation (Cheng et al., 2004; Janakiraman et al., 2002; Spangenberg et al., 1998; Wang et al., 2001).

While direct gene transfer to protoplasts remain useful for transient expression assay, biolistic and *Agrobacterium*-mediated transformation are the two major methods for generating transgenic plants in monocots (Cheng et al., 2004; Janakiraman et al., 2002; Wang et al., 2001). *Agrobacterium*-mediated transformation has received more attention in recent years, because it has the advantage of allowing for the stable integration of a defined DNA segment into the plant genome and generally results in a lower copy number, fewer rearrangements and an improved stability of expression over generations than the free DNA delivery methods (Dai et al., 2001; Hu et al., 2003).

Callus culture has been an inevitable step in monocot and other plant transformation protocols. In many transformation protocols, calluses were used as direct target for microprojectile bombardment or for *Agrobacterium* infection (Cheng et al., 2003; Cho et al., 2001; Hartman et al., 1994; Li and Qu, 2004; Sallaud et al., 2003; Spangenberg et al., 1998; Spangenberg et al., 1995; Vasil et al., 1992; Wan and Lemaux, 1994; Wang et al., 2004; Wang and Ge, 2005). In other protocols, freshly isolated immature embryos or shortly precultured embryos were used as target for microprojectile bombardment or for *Agrobacterium* infection (Aldemita and Hodges, 1996; Frame et al., 2002; Hu et al., 2003; Huber et al., 2002; Popelka and Altpeter, 2003; Tingay et al., 1997; Wan and Lemaux, 1994; Zhao et al., 2000), and calluses were later induced from the bombarded or infected embryos. Callus induction and plant regeneration from the induced callus is not only time consuming and laborious, but also causes somaclonal variation (Choi et al., 2000; Goldman et al., 2004; Spangenberg et al., 1998). Thus, there remains a need for improved methods of *Agrobacterium*-based transformation.

SUMMARY OF THE INVENTION

In accordance with the present invention, there is provided a method of transforming a stolon-producing plant comprising contacting a stolon of the plant with an *Agrobacterium* comprising a recombinant DNA. The stolon may be contacted with the *Agrobacterium* without first forming a callus culture of cells from the stolon. The stolon may be excised from the plant prior to contacting the stolon with the *Agrobacterium*. The plant may be a monocotyledonous plant or a dicotyledonous plant. Stolon-producing monocots include, for example, Kentucky bluegrass (*Poa pratensis*), red fescue (*Festuca rubra*), buffalograss (*Buchloe dactyloides*), St. Augustine grass (*Stenotaphrum secundatum*), zoysiagrass (*Zoysia japonica*), colonial Bentgrass (*Agrostis capillaries*), redtop (*Agrostis gigantea*), western wheatgrass (*Pascopyrum smithii*), sheep fescue (*Festuca ovina*), Canada bluegrass (*Poa compressa*), bog bluegrass (*Poa leptocoma*), wood bluegrass (*Poa nemoralis*), fowl bluegrass (*Poa palustris*), rough bluegrass (*Poa trivialis*), switchgrass (*Panicum virgatum*) and centipedegrass (*Eremochloa ophiuroides*). Stolon-producing dicots include, for example, White clover (*Trifolium repens*), strawberry (*Fragaria*), sweet potato (*Ipomoea batatas*), and potato (*Solanum tuberosum*). The monocotyledonous plant may be sterile, for example, a triploid sterile hybrid turfgrass cultivar.

The recombinant DNA may comprise an expression cassette comprising a promoter active in cells of said plant operably linked to a heterologous coding sequence. The coding region may encode a polypeptide, antisense construct or siRNA construct. Exemplary polypeptides comprise a herbicide resistance polypeptide, an insect resistance polypeptide, a disease resistance polypeptide, a selectable marker polypeptide or a screenable marker polypeptide. The selectable marker may confer resistance to a selective agent, and the method may further comprise contacting the stolon with the selective agent. The recombinant DNA may be a binary vector. The promoter may be a constitutive promoter, inducible promoter or tissue specific promoter. The method may further comprising culturing said stolon on growth media to obtain a transgenic plant, and the transgenic plant may be formed without producing a callus. The method may further comprise planting said plant in soil, and may even further comprise growing said plant to sexual maturity and obtaining a transgenic seed therefrom.

In another embodiment, there is provided a transgenic $T_0$ stolon prepared according to the methods described above. Also provided is a transgenic $T_0$ plant prepared according to the methods described above. In yet a further embodiment, there is provided an isolated stolon of a stolon-producing plant comprising $R_0$ cells transformed with *Agrobacterium* nucleic acid sequences. In still yet a further embodiment, there is provided a method of producing food for human or animal consumption comprising (a) preparing a transgenic plant according to the methods provided above; (b) growing said plant under growth conditions to produce plant tissue from said plant; and (c) preparing food for human or animal consumption from said plant tissue. Preparing food may comprise harvesting said plant tissue. The food may be hay, starch, protein, meal, flour or grain.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." "About" means plus or minus 5% of the stated value.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIGS. 1A-M—Rapid and direct production of transgenic bermudagrass and creeping bentgrass plants from stolon nodes after *Agrobacterium tumefaciens*-mediated transformation. (FIG. 1A) Transient GUS expression three days after co-cultivation of bermudagrass stolon nodes with *Agrobacterium*. (FIG. 1B) GUS expression in regenerating bud of bermudagrass one week after transformation. (FIGS. 1C-E) Green and albino shoots of bermudagrass produced 3 to 4 weeks after hygromycin selection. (FIG. 1F) Rooted transgenic plantlets obtained 6 to 7 weeks after transformation. (FIG. 1G) GUS staining of transgenic (left) and control (right) shoots. (FIG. 1H) GUS staining of transgenic (left) and control (right) leaves. (FIG. 1I) Greenhouse-grown transgenic bermudagrass plants. (FIG. 1J, FIG. 1K) Green shoots of creeping bentgrass produced 3 to 4 weeks after hygromycin selection. (FIG. 1L) GUS staining of transgenic (left) and control (right) leaves. (FIG. 1M) Greenhouse-grown transgenic creeping bentgrass plants.

FIGS. 2A-C—Molecular characterization of transgenic bermudagrass. (FIG. 2A) Polymerase Chain Reaction (PCR) screening of DNA samples from greenhouse-grown plants. Ctrl: untransformed plants serving as control. Arrows indicate the expected hph and gusA bands. (FIG. 2B) Southern hybridization of DNA blot containing BstX I (B) and Xho I (X) digested genomic DNA isolated from greenhouse-grown plants and hybridized with hph probe. (FIG. 2C) Northern blot hybridization using total cellular RNA samples isolated from leaves of transgenic bermudagrass plants and hybridized with the hph probe. Arrow indicates the expected hph transcript.

FIGS. 3A-C—Molecular characterization of transgenic creeping bentgrass. (FIG. 3A) Polymerase Chain Reaction (PCR) screening of DNA samples from greenhouse-grown plants. Ctrl: untransformed plants serving as control. Arrows indicate the expected hph and gusA bands. (FIG. 3B) Southern hybridization of DNA blot containing Hind III digested genomic DNA isolated from greenhouse-grown plants and hybridized with hph probe. (FIG. 3C) Northern blot hybridization using total cellular RNA samples isolated from leaves of transgenic creeping bentgrass plants and hybridized with the hph probe. Arrow indicates the expected hph transcript.

DETAILED DESCRIPTION OF THE INVENTION

The present inventors now report a rapid method for the production of transgenic plants without the requirement of forming a callus. Compared to previous methods, the procedures described allow direct regeneration from stolons and thus significantly reduce the time required to produce transgenic plants. The bypass of callus formation also decreases labor and complications associated with tissue culture, while allowing an even higher transformation efficiency.

In biolistic transformation of bermudagrass, for example, callus induction and maintenance typically takes at least 6 weeks, and the recovery of resistant calluses after bombardment and selection require a minimum of 8 weeks (Li and Qu, 2004; Zhang et al., 2003). It takes at least 20 weeks from callus induction to the regeneration of rooted plantlets (Goldman et al., 2004; Li and Qu, 2004; Zhang et al., 2003). Similarly, the time required for the generation of creeping bentgrass plantlets was 19 weeks by biolistic transformation (Dai et al., 2003; Hartman et al., 1994; Xiao and Ha, 1997) and 22 weeks by *Agrobacterium*-mediated transformation (Luo et al., 2004) when callus culture was involved. In contrast, the techniques reported here allowed production of rooted plantlets in bermudagrass and creeping bentgrass in merely 6 to 7 weeks, e.g., only ⅓ of the time required for other reported transformation systems.

To date, microprojectile bombardment of calluses has been the only reported method for generating transgenic bermudagrass plants (Goldman et al., 2004; Li and Qu, 2004; Zhang et al., 2003). Transgenic creeping bentgrass has been obtained by microprojectile bombardment or *Agrobacterium*-mediated transformation of embryogenic calluses (Hartman et al., 1994; Yu et al., 2000; Zhong et al., 1994). The inventors have now used stolon nodes as explants and successfully bypassed callus formation phase by direct infection of stolon nodes with *Agrobacterium* followed by direct and rapid regeneration of transgenic plants. This appears to be the first report of direct and rapid production of transgenic plants without callus formation in monocot species.

The identification and propagation of compact, yellowish/whitish, embryogenic calluses has been considered a key factor for successful transformation of bermudagrass, creeping bentgrass and other monocot species (Li and Qu, 2004; Luo et al., 2004; Spangenberg et al., 1998; Xiao and Ha, 1997; Zhang et al., 2003). It is known that the selective use of highly embryogenic calluses makes the transformation of grasses an art that also depends upon parameters beyond experimental control (Potrykus, 1991; Spangenberg et al., 1998). Therefore, bypassing the callus formation stage not only saves time, but also simplifies the procedure and makes it more reproducible.

When callus is used for transformation, the final transformation efficiency depends on the frequency of embryogenic callus formation, the percentage of resistant calluses obtained after antibiotic selection, as well as the frequency of plant regeneration from the resistant calluses. Because not all the above information is readily available in the literature, it is difficult to calculate and compare with the final transformation efficiency in the previous reports. However, when compared with the inventors' own callus-based transformation systems for fescues (Spangenberg et al., 1998; Wang et al., 2003a; Wang and Ge, 2005), ryegrasses (Spangenberg et al., 1998; Ye et al., 1997), Russian wildrye (Wang et al., 2004; Wang et al., 2002), bermudagrass and creeping bentgrass, the direct transformation and regeneration protocol reported here is much more efficient. There is also no need for laborious maintenance of callus cultures and cell lines.

Like bermudagrass and creeping bentgrass, many forage and turf grasses are outcrossing and highly heterozygous, individual seeds/embryos from the same cultivar may represent different genotypes. When calluses are induced from different seeds/embryos, it would be impossible to exclude genotypic effects in the regenerants or transformants (Wang et al., 2003a; Wang et al., 2004). Although the use of single genotype-derived cell suspension culture could solve this problem (Spangenberg et al., 1998; Wang et al., 2001), again, it requires considerable time, experience and labor to establish and maintain highly embryogenic suspension cultures (Wang et al., 2003b; Wang et al., 2002). The use of stolons as explants for direct transformation could easily allow the generation of transformants from the same genotype, thus excluding possible genotypic effects in the regenerants and allowing for strict comparison and evaluation of transgene effects in a uniform background.

The techniques described are particularly useful for triploid hybrid bermudagrass (*Cynodon dactylon*×*C. transvaalensis*), Zoysiagrass (*Zoysia japonica*) and creeping bentgrass (*Agrostis stolonifera*). Bermudagrass is widely used as warm-season (C4) forage and turf grass throughout tropical and temperate regions of the world (Li and Qu, 2004). Zoysiagrass is one of the most important turfgrass species in Far-East Asia, its use is rapidly expanding in the USA and other countries (Toyama et al., 2003). Creeping bentgrass is a cool-season (C3) species best known for its fine texture and adaptation to close mowing, which makes it well suited for use on high quality golf course greens (Warnke, 2002). There are dozens of grass species that spread by stolons and rhizomes. This transformation technique should be applicable to these species. In addition, many grass and cereals have high tillering capacity; a modification of the procedure by directly transforming tiller-forming tissues may also have potential for direct and effective generation of transgenics.

Improvement of forage and turf grasses by conventional breeding is slow due to the genetic complexity of these species (Ha et al., 1992; Spangenberg et al., 1998). However, they can be excellent targets for biotechnological improvement because of the unique characteristics of many of these species. For example, the commercial production of bermudagrass is by vegetative propagation of sprigs; therefore, a transgenic line with desired agronomic traits have the potential to be directly propagated and used as a cultivar for commercial purposes. This will avoid problems with seed production (crossing, segregation, level of expression in the progenies) and allow a much quicker release of cultivars. Furthermore, the use of triploid sterile hybrid cultivars could eliminate the pollen or seed-mediated transgene flow problem occurring in most other transgenic plants (Zhang et al., 2003). One of the major constrains of forage-type bermudagrass for animal production is the relatively low digestibility of forage tissues, genetic manipulation of lignin biosynthesis by antisense suppression of endogenous genes (Chen et al., 2003; Chen et al., 2004) may lead to increased digestibility of transgenic plants, which could have tremendous impact on animal productivity in the Southern Great Plains of the United States.

With the availability of more and more EST (expressed sequence tag) sequence information in grasses, as well as simplified molecular cloning techniques, gene isolation has become easier than ever before, the test of gene functions in transgenic plants has become the bottleneck. Thus, the development of an efficient *Agrobacterium*-mediated transformation system for grasses opens up new opportunities for functional characterization of genes and promoters.

In summary, the inventors have developed a straightforward and efficient transformation protocol based on direct shoot regeneration of *Agrobacterium*-infected stolon nodes. The callus-free protocol has been successfully tested in warm-season species, bermudagrass and zoysiagrass, and a cool-season species, creeping bentgrass. Rapid production of rooted transgenic plantlets was achieved in a mere 7 weeks, and transformation efficiencies were up to 6.1% for bermudagrass and 11.3% for creeping bentgrass. This is a significant improvement for genetic transformation of monocot species. However, the methods of the present invention may also be applied advantageously to stolon-producing dicots as well. Specific details on the practice of the present invention are set forth below.

I. TRANSFORMATION

A. *Agrobacterium*

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells generally is well known in the art. See, for example, the methods described by Fraley et al. (1985), Rogers et al. (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

The following patents relate to *Agrobacterium* transformation methods and are hereby incorporated by reference: U.S. Pat. Nos. 6,846,971, 6,822,144, 6,800,791, 6,759,573, 6,696, 622. 6,686,515, 6,664,108, 6,620,986, 6,603,061, 6,455,761, 6,420,630, 6,384,301, 6,369,298, 6,323,396, 6,307,127, 6,300,545, 6,274,791, 6,265,638, 6,255,559, 6,255,115, 6,215,051, 6,162,965, 6,103,955, 6,074,877, 6,074,876, 6,051,757, 6,040,498, 6,037,522, 5,994,624, 5,981,840, 5,977,439, 5,952,543, 5,948,956, 5,932,782, 5,929,300, 5,922,928, 5,919,919, 5,846,797, 5,824,877, 5,824,872, 5,750,871, 5,733,744, 5,712,112, 5,693,512, 5,689,053, 5,591,616, 5,589,615, 5,569,834, 5,565,347, 5,563,055, 5,530,182, 5,463,174, 5,416,011, 5,262,316, 5,188,958, 5,159,135, 5,004,863, 4,954,442, and 4,795,855.

B. Stolons and Stolon-Producing Plants

A stolon is a specialized type of horizontal above-ground shoot, a colonizing organ that arises from an axillary bud near the base of the plant. The stolon differs from the typical vegetative shoot of that same plant in having much longer and, typically, thinner internodes, and the horizontal stolon also has a strong tendency to form adventitious roots at the nodes. A mother plant produces stolons often in several compass directions, permitting cloning, i.e., vegetative reproduction, by producing young ramets (plantlets) around the plant. The stolon, connecting mother plant with each ramet, initially provides the pathway for a flow of nutrients and water to the new plantlet, or even some nutrients from the plantlet back to the mother plant, but that physical connection is eventually severed or becomes dysfunctional as the plantlet develops its nutritional independence. After the stolons are severed, a mother plant is encircled by satellite plantlets, which soon grow larger, filling in any space between the plants. In this way, stoloniferous species usually colonize open ground by forming a continuous ground cover, and thereby can exclude other species by crowding them out. If the plant is lying on the substrate but does not form adventitious roots, the growth habit is termed procumbent. If the plant is lying on the substrate and forms adventitious roots, the growth habit is termed either repent or stoloniferous. Using the term stoloniferous generally requires that the plant must have two different types of vegetative shoots, not only one type, the creeping shoot.

Stoloniferous plants are generally found in habitats where water is abundant or soil is very wet during the season when stolons are formed. For example, one notable California wetland species that spreads via stolons is yerba mansa, *Anemopsis californica* (Family Saururaceae). Widespread stoloniferous herbs of wet habitats are the buttercup *Ranunculus flammula* (Family Ranunculaceae) and mudwort, *Limosella subulata* (Family Scrophulariaceae). Among aquatic plants are the highly successful floating aquatic water hyacinth, *Eichhornia crassipes* (Family Pontederiaceae), in which thick, white stolons enable this species to clone at an alarming high rate. Other wideranging and highly competitive stoloniferous floating aquatics are water soldier (*Stratiotes aloides*) (Hydrocharitaceae), water lettuce (*Pistia stratiotes*, Family Araceae), *Hydrocharis morsus-ranae* (Hydrocharitaceae), and *Potentilla palustris* (Family Rosaceae). Wetlands also may include marsh claytonia (*Claytonia palustris*, Family Portulacaceae), tinker's penny (*Hypericum anagalloides*, Family Hypericaceae), and the fireweed *Epilobium palustre* (Family Onagraceae). *Myosotis scorpioides* is a stolon-like plant of shallow water. In tidal coastal salt marsh, the fleshy *Jaumea carnosa* and the saltgrass *Distichlis spicata* both may spread via stolons.

In addition to species of strawberry (*Fragaria*), other stoloniferous herbs of the rose family (Rosaceae) can be found. Species that appear in the flora of California are Indian strawberry (*Duchesnea indica*) and *Geum reptans*. Rosaceous stoloniferous herbs are successful in a variety of habitats, including sand dunes and wet mountain meadows. Acaena can be a colonizer of new habitats via stolons. Woodland and high elevation habitats may have stoloniferous species of pussytoes, *Antennaria* (Family Asteraceae). In the far Southern Hemisphere, e.g., in Patagonia, can be found the small-leaved stoloniferous species of *Gunnera*, e.g., *G. magellanica*. *Saxifraga stolonifera* (Family Saxifragaceae) is an interesting shade-loving woodland perennial that forms thin red stolons during spring growth. The cultivated white or Irish potato (*Solanum tuberosum*, Family Solanaceae) forms its edible tuber at the tip of a stolon. The stolons grows from an axillary bud at the base of the shoot, and its tip, forming a tuber, becomes buried in the leaf litter and loose soil around the plant, where the tuber develops. Hens and chickens, *Sempervivum* (Family Crassulaceae), form dense mats of leaf succulent rosettes via stolons.

Grass species commonly used as turfgrass are stoloniferous, and they also spread via aggressive creeping rhizomes. Examples include bermudagrass, *Cynodon dactylon*, St. Augustine grass, *Stenotaphrum secundatum*, some species of bluegrass, including the widely planted Kentucky bluegrass, an annual, *Poa annua*, *P. macrantha*, *P. douglasii*, and *P. confinus*. *Poa palustris* is a stoloniferous species growing along California streams and in wet meadows. *Agrostis stolonifera*, creeping bent grass, is, true to its name, stoloniferous. *Melica asperifolia* is a creeping grass of alkaline meadows and seeps around hot springs. Lawns can be formed by the stolon-producing Dichondra, a dicotyledon. Several other dicotyledons herbs found in the lawns of North America spread via stolons, including a weedy sorrel, *Oxalis cornicu-*

*latus* and the nitrogen-fixing white clover, *Trifolium repens*. Other stoloniferous species include clump-forming species of *Episcia* (Family Gesneriaceae) in tropical forests or *Shortia* (Family Diapensiaceae) in cool temperate areas.

II. PLANT TRANSFORMATION CONSTRUCTS, NUCLEIC ACIDS AND POLYPEPTIDES

Various coding sequences may be provided operably linked to a heterologous promoter, in either sense or antisense orientation. *Agrobacterium* expression constructs (above) are provided comprising such sequences, as are plants and plant cells transformed with the sequences. The construction of *Agrobacterium* vectors which may be employed in conjunction with plant transformation techniques using these or other sequences according to the invention will be known to those of skill of the art in light of the present disclosure. The techniques of the current invention are thus not limited to any particular nucleic acid sequences, and the following merely provide examples of genes suitable for transfer and expression into plants.

A. Genes i. Lignin Biosynthesis

One example of a beneficial modification that may be made to plants is to lignin content. Lignin is a major structural component of secondarily thickened plant cell walls. It is a complex polymer of hydroxylated and methoxylated phenylpropane units, linked via oxidative coupling (Boudet et al., 1995). Because of the negative effects of lignin on forage quality, there is considerable interest in genetic manipulation to alter the quantity and/or quality of the lignin polymer (Dixon et al., 1996). At the same time, lignin is important for stem rigidity and hydrophobicity of vascular elements, and, particularly in cereal crops, may be an important inducible defensive barrier against fungal pathogen attack (Beardmore et al., 1983). Thus, lignin modification must not compromise basic functions for the plant and thereby result in negative traits such as lodging or disease susceptibility.

Examples of genes that may be modified include enzymes of the monolignol pathway, such as caffeic acid 3-O-methyltransferase (COMT), caffeoyl CoA 3-O-methyltransferase (CCoAOMT) and cinnamyl alcohol dehydrogenase (CAD). Constitutive cauliflower mosaic virus 35S promoter-driven antisense reduction of COMT to less than 5% of wild-type values in the tropical pasture legume *Stylosanthes humilis* resulted in a strong reduction in S lignin based on histochemical analysis, for example (Rae et al., 2001). In vitro digestibility of stem material in rumen fluid was increased by up to 10% in the transgenic plants exhibiting strongest COMT down-regulation.

ii. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al. (1988); Gleen et al. (1992) and Miki et al. (1990).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah et al., which discloses the nucleotide sequence of a form of EPSPS which can confer glyphosate resistance. Examples of specific EPSPS transformation events conferring glyphosate resistance are provided by U.S. Pat. No. 6,040,497.

A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. DeGreef et al. (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acct-S1, Accl-S2 and Acct-S3 genes described by Marshall et al. (1992).

Genes are also known conferring resistance to a herbicide that inhibits photosynthesis, such as a triazine (psbA and gs+ genes) and a benzonitrile (nitrilase gene). Przbila et al. (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (1992).

iii. Male Sterility

Genes conferring male sterility include those disclosed in U.S. Pat. Nos. 3,861,709, 3,710,511, 4,654,465, 5,625,132, and 4,727,219, each of the disclosures of which are specifically incorporated herein by reference in their entirety. The use of herbicide-inducible male sterility genes is described in U.S. Pat. No. 6,762,344. Male sterility genes can increase the efficiency with which hybrids are made, in that they eliminate the need to physically emasculate the corn plant used as a female in a given cross.

Where one desires to employ male-sterility systems, it may be beneficial to also utilize one or more male-fertility restorer genes. With these genes, male sterile plants can then be efficiently employed as the female parent in hybrid crosses with the restorer line, without the need for physical emasculation of the male reproductive parts of the female parent. The presence of a male-fertility restorer gene results in the production of fully fertile $F_1$ hybrid progeny. If no restorer gene is present in the male parent, male-sterile hybrids are obtained. Examples of male-sterility genes and corresponding restorers which could be employed are well known to those of skill in the art of plant breeding and are disclosed in, for instance, U.S. Pat. Nos. 5,530,191, 5,689,041, 5,741,684, and 5,684,242, the disclosures of which are each specifically incorporated herein by reference in their entirety.

iv. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al. (1994) (cloning of the tomato Cf-9 gene for resistance to *Cladosporium fulvum*); Martin et al. (1993) (tomato Pto gene for resistance to *Pseudomonas syringae* pv.); and Mindrinos et al. (1994) (*Arabidopsis* RSP2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al. (1993), who show that transgenic plants expressing recombinant antibody genes are protected from virus attack. Logemann et al. (1992), for example, disclose transgenic plants expressing a barley ribosome-inactivating gene have an increased resistance to fungal disease.

v. Insect Resistance

One example of an insect resistance gene includes a *Bacillus thuringiensis* protein, a derivative thereof or a synthetic polypeptide modeled thereon. See, for example, Geiser et al. (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al. (1987) (nucleotide sequence of rice cysteine proteinase inhibitor), Huub et al. (1993) (nucleotide sequence of cDNA encoding tobacco proteinase inhibitor I), and Sumitani et al. (1993) (nucleotide sequence of *Streptomyces nitrosporeus* α-amylase inhibitor). An insect-specific hormone or pheromone may also be used. See, for example, the disclosure by Hammock et al. (1990), of baculovirus expression of cloned juvenile hormone esterase, an inactivator of juvenile hormone.

Still other examples include an insect-specific antibody or an immunotoxin derived therefrom and a developmental-arrestive protein. See Taylor et al. (1994), who described enzymatic inactivation in transgenic tobacco via production of single-chain antibody fragments.

vi. Modified Fatty Acid, Phytate and Carbohydrate Metabolism

Genes may be used conferring modified fatty acid metabolism. For example, stearyl-ACP desaturase genes may be used. See Knutzon et al. (1992). Various fatty acid desaturases have also been described, such as a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al., 1993); Δ6- and Δ12-desaturases from the cyanobacteria *Synechocystis* responsible for the conversion of linoleic acid (18:2) to gamma-linolenic acid (18:3 gamma) (Reddy et al., 1993); a gene from *Arabidopsis thaliana* that encodes an omega-3 desaturase (Arondel et al., 1992); plant Δ9-desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al. (1993), for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al. (2000).

A number of genes are known that may be used to alter carbohydrate metabolism. For example, plants may be transformed with a gene coding for an enzyme that alters the branching pattern of starch. See Shiroza et al. (1988) (nucleotide sequence of *Streptococcus* mutants fructosyltransferase gene), Steinmetz et al. (1985) (nucleotide sequence of *Bacillus subtilis* levansucrase gene), Pen et al. (1992) (production of transgenic plants that express *Bacillus licheniformis* α-amylase), Elliot et al. (1993) (nucleotide sequences of tomato invertase genes), Sergaard et al. (1993) (site-directed mutagenesis of barley α-amylase gene), and Fisher et al. (1993) (maize endosperm starch branching enzyme II). The Z10 gene encoding a 10 kD zein storage protein from maize may also be used to alter the quantities of 10 kD Zein in the cells relative to other components (Kirihara et al., 1988).

B. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Llewellyn et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of an acid phosphatase coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots.

C. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of an acid phosphatase coding sequence is used. Alternatively, a heterologous 3' end may enhance the expression of sense or antisense acid phosphatase coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

D. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

E. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. SELECTION, PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population for example, a stolon, by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide LIBERTY™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987), *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene. Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. BREEDING PLANTS OF THE INVENTION

In addition to direct transformation of a particular plant genotype with a construct prepared according to the current invention, transgenic plants may be made used in crosses with a transformed plant having a selected DNA being crossed with a second plant. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:
(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. DEFINITIONS

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Stolon: A stolon is a specialized type of horizontal aboveground shoot, a colonizing organ that arises from an axillary bud near the base of the plant. The stolon differs from the typical vegetative shoot of that same plant in having much longer and, typically, thinner internodes, and the horizontal stolon also has a strong tendency to form adventitious roots at the nodes.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Stolon Transformation of Bermudagrass and Creeping Bentgrass

Plant material. A triploid hybrid bermudagrass (*Cynodon dactylon*×*C. transvaalensis*) cultivar, TifEagle (Hanna and Elsner, 1999), and a creeping bentgrass (*Agrostis stolonifera* L.) cultivar, Penncross, were used in the study. Plants were grown in the greenhouse with 16 h light (390 µm$^{-2}$ s$^{-1}$). Stolons were collected from the plants and cut into 2 to 3 cm segments with nodes in the middle of the segments. The segments were sterilized in 70% ethanol for 1 min and 20% bleach for 10 min and then rinsed three times with sterile water. The nodes were cut in half and the small segments (0.5 to 1.0 cm) each containing a cut node were directly used for *Agrobacterium* infection.

Infection and co-cultivation of stolon nodes with *Agrobacterium tumefaciens*. The *A. tumefaciens* strain EHA105 harboring pCAMBIA 1301 and pCAMBIA 1304 and the LBA4404 strain harboring pTOK233 were used for transformation. All the binary vectors carry a chimeric hygromycin phosphotransferase gene (hph) and a β-glucuronidase gene (gusA). *A. tumefaciens* cultures were grown at 28° C. in liquid AB medium (Chilton et al., 1974) with shaking (200 rpm) till OD$_{600}$ reached 1.0-1.2. Cells were then pelleted by centrifugation at 2400 g for 15 min and resuspended in BG-A1 medium containing half-strength MS medium (Murashige and Skoog, 1962) supplemented with 4.5 µM kinetin, 1.8 µM 2,4-D, 3.3 mM L-cysteine, 1 mM dithiothreitol, 1 mM Na-thiosulfate and 2% (w/v) sucrose. The density (OD$_{600}$) of the resuspended *Agrobacterium* was adjusted to about 1.0, and 0.5 ml of freshly prepared tobacco juice (obtained by squeezing sterile leaves) was added to 30 ml *Agrobacterium* suspension. The stolon nodes were immersed in *Agrobacterium* suspension in culture vessels and vacuum was drawn for 10 min. After vacuum was released, the stolon nodes were incubated with *Agrobacteria* for 50 min with gentle shaking. Excess bacteria were removed after the incubation; the stolon nodes were transferred onto solidified BG-A1 medium and placed in the dark at 25° C. for co-cultivation.

Example 2

Selection and Recovery of Transgenic Plants

Two days after co-cultivation, the infected stolon nodes were transferred onto selection medium BG-A2 (MS medium supplemented with 4.5 µM kinetin, 0.2 µM 2,4-D, 2% sucrose, 250 mg/l cefotaxime and hygromycin). The concentrations of hygromycin (PhytoTechnology Laboratories, Shawnee Mission, Kans.) used for selection of bermudagrass and creeping bentgrass were 75 mg/l and 100 mg/l, respectively. Hygromycin resistant green shoots obtained after 4 to 5 weeks of selection were transferred to plastic vessels containing hormone-free half-strength MS medium. All the regenerating cultures were kept at 25° C. in fluorescent light (40 µE m$^{-2}$ s$^{-1}$) at a photoperiod of 16 h in the growth chamber. Plantlets with well-developed roots were transferred to soil and grown under greenhouse conditions (390 µE m$^{-2}$ s$^{-1}$).

Molecular characterization of transgenic plants. Total genomic DNA was isolated from freeze-dried leaf material of greenhouse-grown plants following the CTAB procedure (Lichtenstein and Draper, 1985). Polymerase chain reactions (PCR) were carried out on the greenhouse-grown transformants to amplify the hph and gusA sequences from the transgene. The transgenes hph and gusA were amplified together in the same reaction. The expected PCR products were 375 bp for hph and 634 bp for gusA. The total volume of reaction mixtures was 50 μl, including 400 ng genomic DNA, 5 ng plasmid (serving as control), 0.5 μl of each primer (50 mM) and 47 μl Platinum PCR Supermix (Invitrogen, Carlsbad, Calif.). Cycling parameters began with an initial hot start at 94° C. for 2 min, then 30 cycles of denaturation (94° C.; 40 s), annealing (60° C.; 30 s) and extension (72° C.; 1 min), followed by a final extension of 5 min at 72° C. PCR amplification products were analyzed by electrophoresis in 1% agarose/ethidium bromide gels.

Genomic DNA was digested with BstX I, Hind III and Xho I. The restriction enzymes BstX I and Hind III only cleave once in the binary vectors used and Xho I cut out the hph coding sequence. Twenty microgram DNA was loaded in each lane. Gel electrophoresis and DNA blotting were carried out following standard protocols (Sambrook et al., 1989). Hybridization probes (hph and gusA) were [$^{32}$P] dCTP-labeled using the RadPrime DNA Labeling System (Invitrogen, Carlsbad, Calif.), and the unincorporated nucleotides were removed by passing through the ProbeQuant™ G-50 Micro Columns (Amersham Biosciences, Piscataway, N.J.). Southern hybridizations were performed using QuikHyb® Hybridization Solution (Stratagene, La Jolla, Calif.) according to the manufacture's specifications.

Total RNA was isolated using TRI reagent (Molecular Research Center, Inc., Cincinnati, Ohio) and RNA gel blotting was carried out according to standard protocols (Sambrook et al., 1989). Northern hybridizations were performed using the [$^{32}$P] dCTP-labeled probes following the QuikHyb® Hybridization protocols.

Example 3

Results

Stolon nodes of bermudagrass and creeping bentgrass were co-cultivated with *Agrobacterium tumefaciens*. The widely available pCAMBIA binary vectors bearing chimeric hygromycin phosphotransferase gene (hph) and β-glucuronidase gene (gusA) were used in combination with *Agrobacterium* strain EHA105. The pTOK233 vector in LBA4404 strain, which was first used for the successful generation of transgenic rice (Hiei et al., 1994), was also tested.

Transient GUS expression assay three days after co-cultivation showed blue staining at the wound site of the stolon nodes (FIG. 1A). Positive GUS staining of emerging bud one week after *Agrobacterium* infection revealed more evidence of transformation at the cut site (FIG. 1B).

For stable transformation, the chimeric hph gene was used as selectable marker and hygromycin was used as selection agent. With a selection pressure of 75 mg/L hygromycin for bermudagrass and 100 mg/L hygromycin for creeping bentgrass, some of the infected stolon nodes became necrotic, while others produced green or albino shoots (FIGS. 1C, 1D and 1K). In contrast, multiple green shoots could be easily obtained from stolon nodes of the control when no selection pressure was applied, indicating the selection schemes were effective in inhibiting growth of non-transformants. Green shoots were directly obtained from infected stolons after 4 to 5 weeks of selection with hygromycin (FIGS. 1E, 1J and 1K). Rooted in vitro plantlets were obtained 2 weeks after transferring the green shoots onto rooting medium (FIG. 1F). Soil-grown bermudagrass and creeping bentgrass plants were established in the greenhouse within 9 weeks after *Agrobacterium*-mediated transformation (FIGS. 1I and 1M).

Greenhouse-grown bermudagrass and creeping bentgrass plants were screened by PCR using primers designed to amplify a 375 bp internal hph fragment and a 634 bp internal gusA fragment. Gel electrophoresis of the PCR amplification products revealed in all cases the presence of a 375 bp hph and a 634 bp gusA band of the expected size in the transgenic samples and its absence in the negative control (FIGS. 2A and 3A), indicating that the selection was stringent. Because the hph and gusA primers were designed to amplify fragments with different lengths, the transgenes (hph and gusA) were amplified simultaneously. This procedure not only saved time and chemicals, but also reduced the chance of obtaining false positives.

Transgenic nature of the bermudagrass and creeping bentgrass plants was further confirmed by Southern hybridization analyses. Genomic DNA digested with single-cutter enzymes (only cleave once in the plasmid) was loaded for each sample and hybridized with hph probe (FIGS. 2B and 3B). Hybridization signals corresponding to bands of different molecular weights were observed in the Southern hybridization analyses (FIGS. 2B and 3B). An expected band was also observed when bermudagrass genomic DNA was digested with an enzyme (XhoI) cutting out the coding sequences (FIG. 2B). The results demonstrated that the transgene was integrated in the genome of the independently transformed bermudagrass and creeping bentgrass plants. Although multiple bands were occasionally observed, more than 80% of the transformants had single copy integration.

Expression of the transgenes in transformed bermudagrass and creeping bentgrass was studied by northern hybridization analyses and GUS assay. Northern hybridization analyses performed with total RNA samples isolated from independent transgenic plants revealed the accumulation at variable levels of the expected hph transcript (FIGS. 2C and 3C). GUS staining of the shoots and leaf tissues revealed the expression of gusa in the transgenics (FIGS. 1G-I).

In total, more than 61 transgenic bermudagrass and 148 transgenic creeping bentgrass plants were produced from three experiments (Table 1). Transformation frequency was calculated based on the number of transgenic plants obtained and the number of stolon nodes inoculated. The transformation frequencies were 4.8-6.1% for bermudagrass and 6.3-11.3% for creeping bentgrass, respectively (Table 1). The pCAMBIA vectors offered higher transformation efficiency than the super-binary vector pTOK233.

TABLE 1

Transformation Frequencies of Stolon Nodes in Bermudagrass and Creeping Bentgrass

| Plant species | Binary vector | Agro strain | Number of stolon nodes infected | Number of transgenic plants recovered | Transformation frequency (%) |
|---|---|---|---|---|---|
| Bermuda-grass | pCAMBIA1301 | EHA 105 | 475 | 29 | 6.1 |
| Bermuda-grass | pCAMBIA1304 | EHA 105 | 402 | 20 | 5.0 |
| Bermuda-grass | pTOK233 | LBA4404 | 250 | 12 | 4.8 |
| Creeping bentgrass | pCAMBIA1301 | EHA 105 | 725 | 82 | 11.3 |
| Creeping bentgrass | pCAMBIA1304 | EHA 105 | 605 | 56 | 9.3 |
| Creeping bentgrass | pTOK233 | LBA4404 | 160 | 10 | 6.3 |

Example 4

Stolon Transformation of Zoysiagrass

Plant material. An improved *Zoysia japonica* cultivar, El Toro (University of California 2000), was used in the study. El Toro is an upright growing cultivar that has many beneficial traits and is widely available internationally for various turf purposes. Non-transgenic plants were grown in the greenhouse with 16 h light (390 µE m$^{-2}$ s$^{-1}$). Stolons were collected from the plants and cut into 2-3 cm segments with nodes in the middle of the segments. The segments were sterilized in 70% ethanol for 1 min and 20% bleach for 12 min and then rinsed three times with sterile water. The nodes were cut in half and the small segments (~0.5 cm) each containing a cut node were directly used for *Agrobacterium* infection.

Binary vectors, *Agrobacterium* preparation and genetic transformation. The binary vectors pCAMBIA 1301, pCAMBIA 1304 and pCAMBIA 1305.2 (www.cambia.org) were introduced into *Agrobacterium tumefaciens* strain EHA105 and used for transformation.

*A. tumefaciens* cultures were grown at 28° C. in liquid AB medium (Chilton et al., 1974) with shaking (200 rpm) till OD600 reached 1.0-1.2. Cells were then pelleted by centrifugation at 2400 g for 15 min and resuspended in a simplified BG-A1 medium containing half-strength MS basal medium (Murashige and Skoog 1962) supplemented with 4.5 µM kinetin, 1.8 µM 2,4-D, 3.3 mM L-cysteine and 2% (w/v) sucrose. The density (OD$_{600}$) of the resuspended *Agrobacterium* was adjusted to about 1.0. The stolon nodes were immersed in *Agrobacterium* suspension in culture vessels and vacuum was drawn for 10 min. After the vacuum valve was released and air was let back into the vacuum chamber, the stolon nodes were incubated with *Agrobacterium* for 50 min with gentle shaking. Excess bacteria were removed after the incubation; the stolon nodes were transferred onto the simplified BG-A1 medium solidified with 0.8% (w/v) agar (Agar-Agar Sigma-Aldrich, Inc., St. Louis, Mo.) and placed in the dark at 25° C. for co-cultivation.

Two days after co-cultivation, the infected stolon nodes were transferred onto selection medium BG-A2: MS basal medium supplemented with 4.5 µM kinetin, 0.2 µM 2,4-D, 2% sucrose, 250 mg/l cefotaxime, 75 mg/l hygromycin and 0.8% (w/v) Agar-Agar (Sigma-Aldrich, Inc., St. Louis, Mo.). Several other tissue culture media (MSK, MSO, MTL-1 and TM1) were also tested for co-cultivation and selection in the preliminary experiments. The tested media were: MSK consisted of MS basal medium supplemented with 0.9 µM kinetin and 3% (w/v) sucrose, MSO consisted of hormone-free half-strength MS medium with 1% (w/v) sucrose, MTL-1 comprised of 22.6 µM 2,4-D, 2.2 µM BAP, 3% (w/v) sucrose and TM1 consisted of MS basal medium supplemented with 4.4 µM BAP, 0.5 µM NAA, 3.3 mM L-cysteine and 3% (w/v) sucrose.

Hygromycin resistant green shoots obtained after 4-5 weeks of selection were transferred to plastic vessels containing hormone-free half-strength MS medium. All the regenerating cultures were kept at 25° C. in fluorescent light (140 µE m$^{-2}$ s$^{-1}$) with 16 h light in the growth room. Plantlets with well-developed roots were transferred to soil and grown under greenhouse conditions (16 h light, 390 µE m$^{-2}$ s$^{-1}$).

Results. Under hygromycin selection, both green and albino shoots were directly produced from the infected stolon nodes, although many of the nodes became necrotic and failed to produce any shoots. In some cases, the initially formed shoots became albino, while green buds were formed from the same node. Since only a low level of 2,4-D was used in the BG-A media, no obvious callus formation was observed. The frequency of resistant green shoots formed on BG-A media after five weeks of culture was 10.5-13.7%.

Other media (MSO, MSK, MTL-1 and TM1) containing no hormone or different hormones were also tested in the preliminary studies. A reasonable number of explants (138-153) were placed on each media. Resistant shoots were produced on all the media tested, however, the frequencies of resistant shoots obtained on these media was 9-20% lower than those on the BG-A media, thus BG-A1 and BG-A2 media were used for the transformation experiments.

Green shoots were obtained from infected stolon nodes after 4-5 weeks of selection with hygromycin. Rooted in vitro plantlets were obtained 3-4 weeks after transferring the green shoots onto rooting medium. Soil-grown zoysiagrass plants were established about 3 weeks after transferring the plantlets to the greenhouse. Totally, it took 10-12 weeks to obtain greenhouse-grown zoysiagrass plants after *Agrobacterium*-mediated transformation of stolons.

Southern hybridization analysis was used to confirm the transgenic nature of the greenhouse-grown zoysiagrass plants. Genomic DNA digested with restriction enzyme Hind III (cleaves only once in the plasmid) was loaded for each sample and hybridized with hph probe. Hybridization signals corresponding to bands of different molecular weights were observed in the Southern blot analysis. The results demonstrated that the transgene was stably integrated in the genome of the independently transformed zoysiagrass plants. Out of nine transgenic plants analyzed, six showed single copy integration.

Expression of the transgenes in transformed zoysiagrass was studied by RT-PCR and GUS assay. RT-PCR analysis performed with RNA samples isolated from independent transgenic plants revealed the expected hph band in all cases. In the case of gusA expression, only some of the samples showed gusA band; this is not surprising because the selection pressure was only applied to the hph gene. Blue staining of the shoots and leaf tissues further confirmed the expression of gusA gene in the transgenics that are RT-PCR positive. Twenty transgenic plants were stained with GUS solution, the frequency of GUS positive plants was 45%.

Transformation frequency was calculated based on the number of transgenic plants obtained and the number of stolon nodes infected. The transformation frequencies were in the range of 6.0-6.8%. No obvious difference was observed for the three binary vectors used.

In order to determine whether the regenerated plants could be chimeric, a Southern blot analysis of 3-4 individual tillers from 5 transgenic lines was performed. The tillers from the same transgenic line showed the same hybridization pattern, demonstrating that the transgenic plants were uniform and not chimeric. Furthermore, transgene expression was compared in five individual tillers collected from each transgenic line. RT-PCR analysis of RNA isolated from individual tillers showed no difference in transgene expression for the tillers collected from the same transgenic line. The results further confirmed that the transgenic plants produced were from single transformation events.

Example 5

Stolon Transformation of Bermudagrass without Tissue Culture

The bermudagrass cultivar, TifEagle (Hanna and Elsner, 1999), was used in the study. Plants were grown in the greenhouse with 16 h light ($390\,\mu E\,m^{-2}\,s^{-1}$). Stolons were collected from the plants and were cut in the nodes. The stolon sections with cut nodes were directly used for *Agrobacterium* infection.

The *A. tumefaciens* strain EHA105 harboring pCAMBIA 3301 was used for transformation. The binary vector pCAMBIA 3301 carries a chimeric phosphinothricin acetyltransferase gene (bar) (de Block et al., 1987) and a β-glucuronidase gene (gusA) (Jefferson et al., 1987), both under the control of CaMV 35S promoter. *A. tumefaciens* cultures were grown at 28° C. in liquid AB medium (Chilton et al., 1974) with shaking (200 rpm) till $OD_{600}$ reached 1.0-1.2. Cells were then pelleted by centrifugation at 2400 g for 15 min and resuspended AB medium supplemented with 1.0 mg/L BAP, 2 mg/L NAA and 100 μM acetosyringone. The density ($OD_{600}$) of the resuspended *Agrobacterium* was adjusted to about 1.0, and 0.5 ml of freshly prepared tobacco juice (obtained by squeezing sterile leaves) was added to 30 ml *Agrobacterium* suspension. The stolon sections were immersed in *Agrobacterium* suspension in culture vessels and vacuum was drawn for 10 min. After vacuum was released, the stolon sections were incubated with *Agrobacteria* for 50 min with gentle shaking. After the incubation, the stolon sections were transferred into petri dishes containing filter papers wet with AB medium supplemented with 1.0 mg/L BAP, 2 mg/L NAA and 100 μM acetosyringone. After 1-2 days of co-cultivation, the stolons were directly transferred to soil; the stolons were covered with a thin layer of soil. One week after transfer the infected stolons to soil, the newly formed shoots were sprayed with the herbicide Finale (0.5%). Surviving shoots were sprayed again with the herbicide after another week. Transgenic bermudagrass plants were obtained after the herbicide sprays.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 3,710,511
U.S. Pat. No. 3,861,709
U.S. Pat. No. 4,535,060
U.S. Pat. No. 4,654,465
U.S. Pat. No. 4,727,219
U.S. Pat. No. 4,769,061
U.S. Pat. No. 4,795,855
U.S. Pat. No. 4,810,648
U.S. Pat. No. 4,940,835
U.S. Pat. No. 4,954,442
U.S. Pat. No. 4,975,374
U.S. Pat. No. 5,004,863
U.S. Pat. No. 5,159,135
U.S. Pat. No. 5,188,958
U.S. Pat. No. 5,262,316
U.S. Pat. No. 5,416,011
U.S. Pat. No. 5,463,174
U.S. Pat. No. 5,530,182
U.S. Pat. No. 5,530,191
U.S. Pat. No. 5,545,818
U.S. Pat. No. 5,550,318
U.S. Pat. No. 5,563,055
U.S. Pat. No. 5,563,055
U.S. Pat. No. 5,565,347
U.S. Pat. No. 5,569,834
U.S. Pat. No. 5,589,615
U.S. Pat. No. 5,591,616
U.S. Pat. No. 5,610,042
U.S. Pat. No. 5,625,132
U.S. Pat. No. 5,684,242
U.S. Pat. No. 5,689,041
U.S. Pat. No. 5,689,053
U.S. Pat. No. 5,693,512
U.S. Pat. No. 5,712,112
U.S. Pat. No. 5,733,744
U.S. Pat. No. 5,741,684
U.S. Pat. No. 5,750,871
U.S. Pat. No. 5,824,872
U.S. Pat. No. 5,824,877
U.S. Pat. No. 5,846,797
U.S. Pat. No. 5,919,919
U.S. Pat. No. 5,922,928
U.S. Pat. No. 5,929,300
U.S. Pat. No. 5,932,782
U.S. Pat. No. 5,948,956
U.S. Pat. No. 5,952,543
U.S. Pat. No. 5,977,439

U.S. Pat. No. 5,981,840
U.S. Pat. No. 5,994,624
U.S. Pat. No. 6,037,522
U.S. Pat. No. 6,040,497
U.S. Pat. No. 6,040,498
U.S. Pat. No. 6,051,757
U.S. Pat. No. 6,074,876
U.S. Pat. No. 6,074,877
U.S. Pat. No. 6,103,955
U.S. Pat. No. 6,162,965
U.S. Pat. No. 6,215,051
U.S. Pat. No. 6,255,115
U.S. Pat. No. 6,255,559
U.S. Pat. No. 6,265,638
U.S. Pat. No. 6,274,791
U.S. Pat. No. 6,300,545
U.S. Pat. No. 6,307,127
U.S. Pat. No. 6,323,396
U.S. Pat. No. 6,369,298
U.S. Pat. No. 6,384,301
U.S. Pat. No. 6,420,630
U.S. Pat. No. 6,455,761
U.S. Pat. No. 6,603,061
U.S. Pat. No. 6,620,986
U.S. Pat. No. 6,664,108
U.S. Pat. No. 6,686,515
U.S. Pat. No. 6,696,622
U.S. Pat. No. 6,759,573
U.S. Pat. No. 6,800,791
U.S. Pat. No. 6,822,144
U.S. Pat. No. 6,846,971
Abe et al., *J. Biol. Chem.*, 262:16793, 1987.
Arondel et al., *Science*, 258(5086):1353-1355 1992.
Beachy et al., *Ann. Rev. Phytopathol.*, 28:451, 1990.
Bevan et al., *Nucleic Acids Res.*, 11(2):369-385, 1983.
Callis et al., *Genes Dev.*, 1:1183-1200, 1987.
Chandler et al., *Plant Cell*, 1:1175-1183, 1989.
Chen et al., *Funct. Plant Biol.*, 31:235-245, 2004.
Chen et al., *Plant Biotechnol. J*, 1:437-449, 2003.
Cheng et al., *In Vitro Cell. Dev. Biol.-Plant*, 39, 595-604, 2003.
Cheng et al., *In Vitro Cell. Dev. Biol.-Plant*, 40, 31-45, 2004.
Chilton et al., *Proc. Natl. Acad. Sci. USA*, 71, 3672-3676, 1974.
Cho et al., *Plant Cell Rep.*, 20:318-324, 2001.
Choi et al., *Crop Sci.*, 40:524-533, 2000.
Conkling et al., *Plant Physiol.*, 93:1203-1211, 1990.
Dai et al., *Mol. Breed.*, 7:25-33, 2001.
Dai et al., *Plant Cell Rep.*, 21:497-502, 2003.
DE Appln. 3642 829
De Block et al., *EMBO J.*, 6(9):2513-2518, 1987.
De Block et al., *Plant Physiol.*, 91:694-701, 1989.
Dellaporta et al., In: *Chromosome Structure and Function: Impact of New Concepts*, 18th Stadler Genetics Symposium, 11:263-282, 1988.
Ebert et al., *Proc. Natl. Acad. Sci. USA*, 84:5745-5749, 1987.
Elliot et al., *Plant Molec. Biol.*, 21:515, 1993.
European Appln. 0 242 246
European Appln. 0 333 033
European Appln. 0616644
European Appln. 154 204
Fisher et al., *Plant Physiol.*, 102:1045, 1993.
Fox et al. *Proc. Natl. Acad. Sci. USA*, 90(6):2486-2490, 1993.
Fraley et al., *Bio/Technology*, 3:629-635, 1985.
Frame et al., *Plant Physiol.*, 129:13-22, 2002.
Fromm et al., *Nature*, 319(6056):791-793, 1986.
Gallie et al., *The Plant Cell*, 1:301-311, 1989.
Geiser et al., *Gene*, 48:109, 1986.
Gleen et al., *Plant Molec. Biology*, 18:1185-1187, 1992.
Goldman et al., *Plant Cell Rep.*, 22:553-560, 2004.
Ha et al., *Plant Cell Rep.*, 11:601-604, 1992.
Hammock et al., *Nature*, 344:458, 1990.
Hanna and Elsner, *Crop Sci.*, 39:1258, 1999.
Hartman et al., *Bio/Technology*, 12:919-923, 1994.
Haseloff et al., *Proc. Natl. Acad. Sci. USA*, 94(6):2122-2127, 1997.
Hayes et al., *Biochem. J.*, 285(Pt 1): 173-180, 1992.
Hiei et al., *Plant J.*, 6:271-282, 1994.
Hiei et al., *Plant Mol. Biol.*, 35(1-2):205-218, 1997.
Hinchee et al., *Bio/technol.*, 6:915-922, 1988.
Hu et al., *Plant Cell Rep.*, 21:1010-1019, 2003.
Huber et al., *Mol. Breed.*, 10:19-30, 2002.
Hudspeth and Grula, *Plant Mol. Biol.*, 12:579-589, 1989.
Huub et al., *Plant Molec. Biol.*, 21:985, 1993.
Ikuta et al., *Bio/technol.*, 8:241-242, 1990.
Ishidia et al., *Nat. Biotechnol.*, 14(6):745-750, 1996.
Janakiraman, et al., *In Vitro Cell. Dev. Biol.-Plant*, 38:404-414, 2002.
Jauhar, In: *Cytogenetics of the Festuca-Lolium complex: relevance to breeding*, Springer, Berlin, 1993.
Jones et al., *Science*, 266:7891, 1994.
Ke et al., *Plant Cell Rep.*, 20:150-156, 2001.
Kirihara et al., *Gene*, 71(2):359-370, 1988.
Klee et al., *BioTechnology*, 3(7):637-642, 1985.
Knutzon et al., *Proc. Natl. Acad. Sci. USA*, 89:2624, 1992.
Lawton et al., *Plant Mol. Biol.* 9:315-324, 1987.
Lee et al., *EMBO J.*, 7:1241, 1988.
Li and Qu, *Plant Cell Rep.*, 22:403-407, 2004.
Lichtenstein, and Draper, In: *DNA Cloning, Glover* (Ed.), 67-119. IRL Press, Oxford, 1985.
Llewellyn et al., *J. Mol. Biol.* 195(1):115-23, 1987.
Logemann et al., *Biotechnology*, 10:305, 1992.
Luo et al., *Plant Cell Rep.*, 22:645-652, 2004.
Marshall et al., *Theor. Appl. Genet.*, 83:4:35, 1992.
Martin et al., *Science*, 262: 1432, 1993.
McCormac et al., *Euphytica*, 99(1):17-25, 1998.
McDonough et al., *J. Biol. Chem.*, 267(9):5931-5936, 1992.
Miki et al., *Theor. Appl. Genet.*, 80:449, 1990. Aldemita and Hodges, *Planta*, 199:612-617, 1996.
Mindrinos et al., *Cell*, 78(6):1089-1099, 1994.
Murakami et al., *Mol. Gen. Genet.*, 205:42-50, 1986.
Murashige and Skoog, *Physiol. Plant.*, 15:473-497, 1962.
Ogawa et al., *Sci. Rep.*, 13:42-48, 1973.
Ow et al., *Science*, 234:856-859, 1986.
PCT Appln. WO 91/13972
PCT Appln. WO 97/4103
PCT Appln. WO 97/41228
Pen et al., *Biotechnology*, 10:292, 1992.
Popelka and Altpeter, *Mol. Breed.*, 11:203-211, 2003.
Potrykus et al., *Mol. Gen. Genet.*, 199(2):169-177, 1985.
Potrykus et al., *Mol. Gen. Genet.*, 199:183-188, 1985.
Potrykus, *Annu. Rev. Plant Physiol. Plant Mol. Biol.*, 42:205-225, 1991.
Prasher et al., *Biochem. Biophys. Res. Commun.*, 126(3): 1259-1268, 1985.
Przibila et al., *Plant Cell*, 3:169, 1991.
Raboy et al., *Plant Physiol.*, 124(1):355-368.
Reddy et al., *Plant Mol. Biol.*, 22(2):293-300, 1993.
Reichel et al., *Proc. Natl. Acad. Sci. USA*, 93(12):5888-5893, 1996.
Rogers et al., *Methods Enzymol.*, 153:253-277, 1987.
Sahrawat et al., *Plant Sci.*, 165, 1147-1168, 2003.
Sallaud et al., *Theor. Appl. Genet.*, 106:1396-1408, 2003.

Sambrook et al., In: *Molecular cloning, Cold Spring Harbor Laboratory Press, Cold Spring Harbor, N.Y.*, 1989.
Sambrook et al., In: *Molecular cloning*: a laboratory manual, 2nd Ed., Cold Spring Harbor Laboratory, NY, 1989.
Sergaard et al., *J. Biol. Chem.*, 268:22480, 1993.
Sheen et al., *Plant J.*, 8(5):777-784, 1995.
Shiroza et al., *J. BacteoL.*, 170:810, 1988.
Spangenberg et al., In: *Biotechnology in forage and turf grass improvement*, Springer, Berlin, 1998.
Spangenberg et al., *J. Plant Physiol.*, 145:693-701, 1995.
Spencer et al., *Plant Mol. Biol.*, 18(2):201-210, 1992.
Stalker et al., *Science*, 242:419-422, 1988.
Steinmetz et al., *Mol. Gen. Genet.*, 20:220, 1985.
Sullivan et al., *Mol. Gen. Genet.*, 215(3):431-440, 1989.
Sutcliffe, *Proc. Natl. Acad. Sci. USA*, 75:3737-3741, 1978.
Tavladoraki et al., *Nature*, 366:469, 1993.
Taylor et al., Seventh Int'l Symposium on Molecular Plant-Microbe Interactions, Edinburgh, Scotland, Abstract W97, 1994.
Thillet et al., *J. Biol. Chem.*, 263:12500-12508, 1988.
Thomas et al., *Plant Sci.* 69:189-198, 1990.
Thompson et al., *EMBO J.*, 6(9):2519-2523, 1987.
Tian et al., *Genes Dev.*, 11(1):72-82, 1997.
Tingay et al., *Plant J.*, 11(6):1369-1376, 1997.
Tingay et al., *Plant J.*, 11 (6):1369-1376, 1997.
Toyama et al., *Mol. Cells.* 16:1, pp. 199-27, 2003.
Twell et al., *Plant Physiol.*, 91:1270-1274, 1989.
Van Damme et al., *Plant Molec. Biol.*, 24:25, 1994.
Van Hartingsveldt et al., *Gene*, 127:87, 1993.
Vasil et al., *Bio/Technology*, 10:667-674, 1992.
Vasil et al., *Plant Physiol.*, 91:1575-1579, 1989.
Vasil, *Plant Mol. Biol.*, 25: 925-937, 1994.
Wan and Lemaux, *Plant Physiol.*, 104:37-48, 1994.
Wang and Ge, *J. Plant Physiol.*, 162:103-113, 2005.
Wang et al., *Crit. Rev. Plant Sci.*, 20:573-619, 2001.
Wang et al., *In Vitro Cell. Dev. Biol. Plant*, 39:277-282, 2003a.
Wang et al., *Molec. Cell. Biol.*, 12(8):3399-3406, 1992.
Wang et al., *Plant Cell Rep.*, 20:797-801, 2002.
Wang et al., *Plant Cell Rep.*, 22:903-909, 2004.
Wang et al., *Plant Cell, Tissue Organ Cult.*, 73:265-273, 2003b.
Warnke, In: *Turfgrass biology, genetics and breeding*, Casler and Duncan (Eds), 175-185. John Wiley & Sons, Inc., Hoboken, N.J., 2002.
Xiao et al., *Plant Cell Rep.*, 16:874-878, 1997.
Yang and Russell, *Proc. Natl. Acad. Sci. USA*, 87:4144-4148, 1990.
Ye et al., *Plant Cell Rep.*, 16:379-384, 1997.
Yu et al., *Hereditas*, 133:229-233, 2000.
Zhang et al., *Plant Cell Rep.*, 21:860-864, 2003.
Zhao et al., *Plant Mol. Biol.*, 44:789-798, 2000.
Zhong et al., *Plant Cell Rep.*, 13:1-6, 1994.
Zukowsky et al., *Proc. Natl. Acad. Sci. USA*, 80:1101-1105, 1983.

What is claimed is:

1. A method of transforming a stolon-producing turfgrass plant comprising contacting a stolon of the plant with an *Agrobacterium* comprising a recombinant DNA and selecting a transformed tissue comprising the recombinant DNA, wherein the stolon is contacted with the *Agrobacterium* without first forming a callus culture of cells from the stolon.

2. The method of claim 1, wherein the stolon is excised from the plant prior to contacting the stolon with the *Agrobacterium*.

3. The method of claim 1, wherein the turfgrass plant is a bermudagrass, a creeping bentgrass or a zoysiagrass.

4. The method of claim 1, wherein the turfgrass plant is sterile.

5. The method of claim 1, wherein the turfgrass plant is a triploid sterile hybrid turfgrass cultivar.

6. The method of claim 1, wherein the recombinant DNA comprises an expression cassette comprising a promoter active in cells of said plant operably linked to a heterologous coding sequence.

7. The method of claim 6, wherein said coding sequence encodes a polypeptide, antisense construct or siRNA construct.

8. The method of claim 7, wherein the coding sequence encodes a polypeptide, wherein the polypeptide comprises a herbicide resistance polypeptide, an insect resistance polypeptide, a disease resistance polypeptide, a selectable marker polypeptide or a screenable marker polypeptide.

9. The method of claim 8, wherein the polypeptide comprises a selectable marker that confers resistance to a selective agent.

10. The method of claim 9, further comprising contacting the stolon with the selective agent.

11. The method of claim 1, wherein the recombinant DNA is a binary vector.

12. The method of claim 1, further comprising culturing said stolon on growth media to obtain a transgenic plant.

13. The method of claim 12, wherein the transgenic plant is formed without producing a callus.

14. The method of claim 12, further comprising planting said plant in soil.

15. The method of claim 14, further comprising growing said plant to sexual maturity and obtaining a transgenic seed therefrom.

16. The method of claim 6, wherein said promoter is a constitutive promoter, inducible promoter or tissue specific promoter.

* * * * *